US008304392B2

(12) United States Patent
Dal Farra et al.

(10) Patent No.: US 8,304,392 B2
(45) Date of Patent: Nov. 6, 2012

(54) PHARMACEUTICAL AND/OR COSMETIC COMPOSITION CONTAINING AN ACTIVE PRINCIPLE ACTIVATOR OF CYTOCHROME C

(75) Inventors: Claude Dal Farra, Opio (FR); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 297 days.

(21) Appl. No.: 12/597,857

(22) PCT Filed: Apr. 23, 2008

(86) PCT No.: PCT/FR2008/000578
§ 371 (c)(1),
(2), (4) Date: Oct. 27, 2009

(87) PCT Pub. No.: WO2008/145855
PCT Pub. Date: Dec. 4, 2008

(65) Prior Publication Data
US 2011/0123466 A1    May 26, 2011

(30) Foreign Application Priority Data

Apr. 27, 2007 (FR) ...................................... 07 03057

(51) Int. Cl.
| | |
|---|---|
| *A61K 38/08* | (2006.01) |
| *A61K 38/07* | (2006.01) |
| *A61K 38/06* | (2006.01) |
| *A61Q 17/04* | (2006.01) |
| *A61Q 19/00* | (2006.01) |
| *A61Q 19/08* | (2006.01) |
| *C07K 5/08* | (2006.01) |
| *C07K 5/10* | (2006.01) |
| *C07K 7/00* | (2006.01) |
| *C07K 7/06* | (2006.01) |

(52) U.S. Cl. .................... 514/21.8; 514/18.6; 514/18.8; 514/21.9; 530/330; 530/331

(58) Field of Classification Search ........................ None
See application file for complete search history.

(56) References Cited

U.S. PATENT DOCUMENTS
| | | | |
|---|---|---|---|
| 2006/0013794 A1 | 1/2006 | Dal Farra et al. | |
| 2007/0060521 A1 * | 3/2007 | Jove et al. ....................... | 514/12 |
| 2008/0227725 A1 | 9/2008 | Dal Farra et al. | |

FOREIGN PATENT DOCUMENTS
| | | |
|---|---|---|
| EP | 1864996 A | 12/2007 |
| WO | 0063236 A | 10/2000 |
| WO | 0208752 A | 1/2002 |
| WO | 0226254 A | 4/2002 |
| WO | 0246416 A | 6/2002 |
| WO | 2004/043482 A | 5/2004 |
| WO | 2005/097060 A | 10/2005 |
| WO | 2007058625 A | 5/2007 |

OTHER PUBLICATIONS

Definition of derivative and analogs from http://cancerweb.ncl.ac.uk/omd/about.html, pp. 1-5. Accessed Jul. 7, 2005.*
Chronic Effects of Sunlight from Merck Manual, pp. 1-2. Accessed Mar. 21, 2012.*
Disorders of Neuromuscular Transmission from Merck Manual, pp. 1-2. Accessed Mar. 21, 2012.*
Age related diseases from Merck Manual, pp. 1-5. Accessed Mar. 21, 2012.*
Diabetes Mellitus (DM) from Merck Manual, pp. 1-15. Accessed Mar. 21, 2012.*
Frankel, Max et al: "'Synthesis of peptides related to the C terminus of horse heart cytochrome c", Colloques Internationaux'Du Centre National De La Recherche Scientifique ,1968, pp. 278-282, No. 175, XP009093273.
Gondran C et al., "A new synthetic peptide that exhibits interesting anti-aging effects", Journal of Investigative Dermatology, Apr. 2006, p. 27, vol. 126, No. Suppl. 1 , XP009093186 & 67th Annual Meeting of the Society for Investigative-Dermatology, May 3-6, 2006, Philadelphia, PA, USA.
Del Farra et al., "Anti-aging effects observed in new synthetic peptide" J Am Acad Dermatol, Feb. 2007, p. AB25, XP002460912.
Del Farra et al., "An anti-aging effect on the lips and skin observed in in vivo studies on a new fibronectin-like peptide", J Am Acad Dermatol, Feb. 2007, p. AB88, XP002460913.
International Search Report in Corresponding Application No. PCT/FR2008/000578 Dated Nov. 10, 2008.

* cited by examiner

*Primary Examiner* — Julie Ha
(74) *Attorney, Agent, or Firm* — Young & Thompson

(57) ABSTRACT

A peptide of formula: $R_1$-$X_1$-$X_2$-$X_3$-$X_4$-$X_5$-$R_2$, wherein $X_1$ is T; $S_2$ is L; $X_3$ is K; $X_4$ is T, S, K, R or no amino acid; $X_5$ is V, A, Y, M or no amino acid; $R_1$ represents a primary amine function of the N-terminal amino acid; and $R_2$ represents a hydroxyl function of the C-terminal amino acid, is capable of activating cytochrome C. The peptide can be included in cosmetic and pharmaceutical compositions intended to stimulate the functions of the mitochondria and increase intracellular ATP levels. Such compositions are useful to help protect the skin from external aggression, reduce and treat skin damage caused by UV radiation and combat cutaneous signs of aging.

18 Claims, No Drawings

PHARMACEUTICAL AND/OR COSMETIC COMPOSITION CONTAINING AN ACTIVE PRINCIPLE ACTIVATOR OF CYTOCHROME C

FIELD OF THE INVENTION

The present invention is in the cosmetic and pharmaceutical domain, and more particularly in the domain of dermatology. The present invention concerns a cosmetic or pharmaceutical composition, and notably a dermatological one, comprising, in a physiologically adapted medium, an active principle capable of activating cytochrome C. This active principle may be composed of polypeptides or of peptides and may be used alone or in association with at least one other active principle. The invention is also related to the use of a cosmetic composition intended to stimulate the functions of the mitochondria and to increase the cellular energy level. The invention also concerns a cosmetic-treatment procedure intended to protect the skin and the appendages from external aggressions and to combat cutaneous aging.

The active principle can also be used to prepare pharmaceutical compositions intended to prevent or combat pathologies linked to mitochondrial dysfunctions, for example, certain neuromuscular or cardiac degenerations, type II diabetes, or even certain pathologies of aging.

BACKGROUND OF THE INVENTION

The term "appendages" according to the invention encompasses the assemblage of keratinic appendices exhibited on the body surface, in particular the hair, eyelashes, eyebrows, nails, and hair.

The skin is a vital organ that covers the entire surface of the body and provides protective, sensitive, immune, metabolic, or even thermoregulatory functions. The skin, like other organs, is subject to aging. So, one of the major mechanisms implicated in the processes of aging is the accumulation of oxidative damage in essential molecules such as membrane lipids, proteins, DNA, and most particularly mitochondrial DNA (DNAmt).

Oxidative damage is caused by free radicals, chemically unstable and very reactive species generated by intracellular metabolism or external aggressions. Among these external aggressions, the following may be cited: UV radiation, toxins, atmospheric pollutants, and alimentary oxidants. Premature aging is observed in the skin, occurring in areas exposed to radiation, characterized by phenomena of alterations in the macromolecules (lipid peroxidation, carbonylation of proteins) affecting, in particular, elastin, collagen, and fibronectin. Progressive decline with age can also be shown in the mitochondrial functions with age, probably linked to the accumulation of mutations on DNAmt (K. Singh (2004), *Ann. NY Acad. Sci.*, 1019).

One of the important consequences of the accumulation of oxidative damage is the reduction in the capacity of the cell to produce ATP (Porteous et al. (1998), *Eur. J. Biochem.* 257(1), 192-201). Thus, the phenomenon of cellular aging is in proportion to oxidative damage which the cell undergoes as well as to the process of producing the energy the cell needs to survive.

The body possesses defense mechanisms capable of trapping or of transforming free radicals (enzymes, glutathione, vitamins A and E, coenzyme Q10, etc.). However, these antioxidant defense systems often prove to be insufficient under the numerous stresses and external aggressions to which the body, and the skin in particular, are subjected.

In this context, the particular properties of cytochrome C appear to be particularly interesting.

Cytochrome C is a small soluble protein, 15 KDa atomic mass, which plays an essential role in mitochondrial function and in cellular survival. Cytochrome C is a molecule retained to a high degree in the majority of the eucaryotes; it is found in the mitochondria of plants, animals, and numerous single-celled organisms. Cytochrome C exhibits a proteinic structure organized around a porphyrin made up of four pyrrole nuclei, themselves linked to an iron atom.

The principal role of cytochrome C is to provide for the transfer of electrons, due to a change in the valence of the iron atom. Cytochrome C, which is soluble, thus transports the electrons from a III coordination compound (coenzyme QH2/cytochrome C reductase) to a IV coordination compound (cytochrome oxidase). The electrons, which are the substrate of cytochrome oxidase, are then transferred by the enzyme to the oxygen.

The search for compounds capable of stimulating the mitochondria and raising the cellular energy level in order to prevent or to combat signs of cutaneous aging or damage caused by external aggressions, such as UV rays, radiation, or exposure to toxins or to pollutants, is an important concern of medical research and of cosmetics. In this regard, solutions have been proposed such as intake of substances implicated in energy metabolism, and more particularly, intermediaries or cofactors of the Krebs cycle such as fumarate, L-malate, acetyl CoA (WO 02064129), or even treating the skin with substances capable of reducing the free radicals, such as vitamin C (US 2004/0086526) or L-ergothionine (WO 9836748). But to the knowledge of the applicant, no cosmetic or pharmaceutical composition including polypeptides or peptides capable of activating cytochrome C has yet been described.

SUMMARY OF THE INVENTION

The inventors have in effect highlighted a cosmetic and therapeutic activity, notably a dermatological one, of polypeptides or of peptides capable of activating cytochrome C. It has been particularly brought out that these polypeptides or these peptides, when they are applied on the skin, stimulate the mitochondrial functions in a significant way. This, among other things, has been demonstrated by an increase in the expression of cytochrome C and an increase in the synthesis of ATP. This new active principle, a stimulator of mitochondria and more generally capable of protecting the skin from external aggressions, thus opens up new therapeutic and cosmetic perspectives.

An "active principle capable of protecting the skin from external aggressions" is understood to be any substance capable of exhibiting protective properties or of reducing the apoptosis of cells or tissues subjected to a stress of physicochemical or environmental origin.

An "active principle capable of activating cytochrome C" is understood to be any substance capable of increasing the expression of cytochrome C, either by activating proteinic synthesis (by means of direct or indirect modulation of the gene expression of cytochrome C), or by increasing the biological activity of cytochrome C, or by other biological processes such as the stabilization of the cytochrome C protein or even the stabilization of the messenger RNA transcripts.

Preferentially, the substances capable of activating cytochrome C according to the invention will be polypeptides or peptides.

Thus, the invention has as its first object a cosmetic or pharmaceutical composition, and in particular a dermatological one, including, in a physiologically adapted medium, peptides capable of activating cytochrome C as an active principle, alone or in association with at least one other active principle.

Preferentially, according to the present invention, the said peptides capable of activating cytochrome C or their biologically active derivatives are peptides whose amino acid number is between 3 and 13.

According to a particularly advantageous method of achieving the invention, the peptides possesses a sequence that answers to the general formula (I)

$$R_1\text{-}(AA)_n\text{-}X_1\text{—}X_2\text{—}X_3\text{—}X_4\text{—}X_5\text{-}(AA)_p\text{-}R_2$$

where
- $X_1$ is tyrosine,
- $X_2$ is leucine,
- $X_3$ is lysine,
- $X_4$ is threonine, serine, arginine, or no amino acid,
- $X_5$ is valine, alanine, tyrosine, methionine, or no amino acid,
- AA represents any amino acid whatever, or one of its derivatives, and n and p are whole numbers between 0 and 4.
- $R_1$ represents the primary amine function of the N-terminal amino acid, free or substituted with a protector group which may be chosen from an acetyl group, a benzoyl group, a tosyl group, or a benzyloxycarbonyl group.
- $R_2$ represents the hydroxyl function of the carboxylic acid of the C-terminal amino acid, free or substituted with a protector group which can be chosen from an alkyl chain of $C_1$ to $C_{20}$, or an $NH_2$, NHY, or NYY group, with Y representing a alkyl chain of $C_1$ to $C_4$.

DETAILED DESCRIPTION OF THE INVENTION

According to one, most especially preferred embodiment of the invention, the biologically active peptide has the sequence:

|  |  |
| --- | --- |
| (SEQ ID No. 1) | Tyr-Leu-Lys-Lys-Ala |
| (SEQ ID No. 2) | Tyr-Leu-Lys-Lys-Ala-NH$_2$ |
| (SEQ ID No. 3) | Tyr-Leu-Lys-Lys-NH$_2$ |
| (SEQ ID No. 4) | Tyr-Leu-Lys |

According to one particularly interesting embodiment, the biologically active peptide corresponds to the sequence SEQ ID No. 1.

According to another particularly interesting embodiment, the biologically active peptide corresponds to the sequence SEQ ID No. 2.

The invention also concerns homologous forms of these sequences. The term "homologous" designates, according to the invention, any peptide sequence identical to at least 50%, or preferably to at least 80%, and even more preferentially to at least 90% of said peptide sequence, chosen from among the sequences SEQ ID No. 1 to SEQ ID No. 4. A "peptide sequence identical to at least X %" is understood to designate a identity percentage between the residues of amino acids of the two sequences to be compared, obtained after the optimal alignment of the two sequences. The optimal alignment is obtained using algorithms for local homologies such as those used by the computer software BLAST P or T BLAST N, available on the National Center for Biotechnology Information (NCBI) website.

The term "homologous" can also designate a peptide that differs from the sequence of a peptide with sequence SEQ ID No. 1 to SEQ ID No. 4 by the substitution of chemically equivalent amino acids, that is, by the substitution of one residue by another possessing the same characteristics. Thus, the classic substitutions are made between Ala, Val, Leu, and Ile; between Ser and Thr; between the acid residues of Asp and Glu; between Asn and Gln; and between the basic residues of Lys and Arg, or between the aromatic residues of Phe and Tyr.

In the invention, the term "amino acid" refers here to any natural or synthetic organic acid having the formula:

$$\text{—NHR—CR—C(O)—O—}$$

where each —R is independently selected from a hydrogen or an alkyl group having between 1 and 12 carbon atoms. Preferentially, at least one group —R of each amino acid is a hydrogen. The term "alkyl" is understood here to be a carbon chain which can be linear or branched, substituted (mono- or poly-) or unsubstituted; saturated, monosaturated (a double or triple bond in the chain) or polyunsaturated (two or several double bonds, two or several triple bonds, one or several double bonds and one or several triple bonds in the chain).

The term "peptide" designates a chaining of two or several amino acids linked to one another by peptide bonds or by modified peptide bonds, the term "polypeptide" designating a peptide of greater size.

"Peptide" must be understood to be the natural or synthetic peptide of the invention as described above or at least one of its fragments, which is either obtained by proteolysis or synthetically, or even any natural or synthetic peptide whose sequence is wholly or partially composed of the sequence of the peptide described previously. So as to improve resistance to degradation, it may be necessary to utilize a protected form of the peptide according to the invention. The form of protection shall of course be a biologically compatible form and shall be compatible with a use in the domain of cosmetics or of pharmaceuticals.

Numerous forms of biologically compatible protection may be envisioned. Thus, the invention concerns a composition as defined previously, characterized by the fact that the peptide with general formula (I) possesses at least one functional group protected by a protector group, this protector group being either an acylation or an acetylation of the amino-terminal end, or an amidation or an esterification of the carboxy-terminal end, or both of these. The amino-terminal end may be protected by an acetyl group, a benzoyl group, a tosyl group, or a benzyloxycarbonyl group. Preferably, a protection is used based on the amidation of the hydroxyl function of the carboxy-terminal end by an NYY group, with Y representing an alkyl chain of $C_1$ to $C_4$, or esterification by an alkyl group. It is also possible to protect both the ends of the peptide.

The peptide derivatives also concern amino acids and peptides connected to one another by a pseudo-peptide bond. A "pseudo-peptide bond" is understood to be any of the types of bond likely to replace the "classic" peptide bonds. In the domain of the amino acids, the geometry of the molecules is such that they can theoretically exhibit the form of different optical isomers. Indeed, there exists one molecular conformation of the amino acid (AA) such that it deflects the plane of light polarization to the right (dextrorotatory or D-aa conformation), and a molecular conformation of the amino acid (aa) such that it deflects the plane of light polarization to the left (levorotatory or L-aa conformation). The natural amino acids are always in the levorotatory conformation. Consequently, a peptide of natural origin will be composed of only amino acids of the L-aa type. However, chemical synthesis in the laboratory enables amino acids to be prepared which have both possible conformations. Starting with this material as a base, it is thus possible during peptide synthesis to incorporate equally well amino acids in the form of dextrorotatory or levorotatory optical isomers. Thus, the amino acids composing the peptide according to the invention may be in the L or D configuration; preferentially, the amino acids are in the L form. The peptide according to the invention can thus be in an L, D, or DL form.

The peptide with general formula (I) according to the invention can be obtained either by classical chemical synthesis (in solid phase or homogeneous liquid phase) or by enzymatic synthesis (Kullman et al. (1980), *J. Biol. Chem.*, 225, 8234), starting from the constituent amino acids or from their derivatives.

The peptide according to the invention can also be obtained by fermentation of a strain of bacteria, modified or not by genetic engineering, or even by extraction of proteins of animal or vegetable origin, preferentially of vegetable origin, followed by a controlled hydrolysis which releases the peptide fragments which correspond in whole or in part to the peptides with general formula (I).

A great many proteins found in plants are likely to contain these sequences within their structure. Controlled hydrolysis enables these peptide fragments to be released. It is possible, but not necessary to achieve the invention, either to extract the proteins concerned first and then to hydrolyze them, or to perform the hydrolysis first on a raw extract and to subsequently purify the peptide fragments. It is also possible to use certain hydrolyzed extracts without purifying the peptide fragments in them which correspond to the general formula (I) according to the invention, but at the same time ensuring the presence of the said fragments by appropriate analytical means.

Other procedures, simpler or more complex, may be envisioned by the professional familiar with the craft of synthesis, extraction, and purification of proteins and peptides. Thus, the peptide according to the invention can be of natural or synthetic origin. Preferentially according to the invention, the peptide is obtained by chemical synthesis.

According to the invention, the active principle can be a mixture of peptide derivatives and/or constituents of amino acid derivatives.

According to one advantageous embodiment of the invention, the active principle according to the invention is solubilized in advance in one or several solvents traditionally used by the professional, such as water, glycerol, ethanol, propylene glycol, butylene glycol, dipropylene glycol, ethoxylated or propoxylated diglycols, cyclic polyols, Vaseline, a vegetable oil, or any mixture of these solvents.

According to yet another advantageous embodiment of the invention, the active principle according to the invention is solubilized in advance in a cosmetic or pharmaceutical vehicle like the liposomes or is adsorbed onto powdered organic polymers or mineral supports like the talcs and bentonites, and is more generally solubilized in, or fixed upon, any cosmetically or pharmaceutically acceptable vehicle.

The composition usable according to the invention can, in particular, consist of a composition for hair care, and particularly a shampoo, a conditioner, a blow-dry lotion, a treatment lotion, a cream or a styling gel, a restructuring lotion for the hair, a mask, etc. The cosmetic composition according to the invention can be used particularly in treatments implementing an application that is followed or not by a rinse, or even in the form of shampoo.

It can also come in the form of a dye or a mascara to be applied with the brush or the comb, in particular on the eyelashes, eyebrows, or hair.

It is of course understood that the active principle according to the invention can be used alone or in association with at least one other active principle, in a cosmetic composition or for the preparation of a pharmaceutical and/or dermatological composition.

The compositions according to the invention could be applied in any appropriate way, particularly oral, parenteral, or externally topical, and their formulation will be adapted by the professional in particular for cosmetic or dermatological compositions. Advantageously, the compositions according to the invention are presented in a form adapted to application by topical means. These compositions shall therefore contain a cosmetologically and/or dermatologically acceptable medium, that is, compatible with the skin and the appendages, and they cover all the cosmetic or dermatological forms. These compositions could, in particular, be in the form of creams, oil-in-water emulsions, or water-in-oil or multiple emulsions, solutions, suspensions, gels, milks, lotions, sticks, or even powders, adapted to an application onto the skin, the lips, and/or the appendages.

These compositions include the excipients necessary for their formulation, such as solvents, thickeners, diluents, surfactants, antioxidants, colorants, preservatives, or perfumes.

Advantageously, the usable compositions contain at least one other active agent promoting the action of the peptides according to the invention. Thus, the composition according to the invention may associate, with the active principle according to the invention, active agents having an antioxidant action, or else stimulating the synthesis of dermal macromolecules, or else stimulating energy metabolism. For example, as active agents having an anti-radical or antioxidant action, vitamin C, vitamin E, coenzyme Q10, and the polyphenolic extracts of plants may be cited.

Active agents stimulating the syntheses of dermal macromolecules (laminin, fibronectin, collagen) may also be cited, for example the collagen peptide marketed under the name of COLLAXYL® by the Vincience Company.

Finally, the active principle marketed under the name of GP4G® by the Vincience Company may be cited among active agents stimulating energy metabolism.

From another angle, the composition according to the invention may be a sun-related composition, that is, a composition that aids in protection against solar radiation. Thus, there may be advantageously added to the composition according to the invention active agents aiding in solar protection such as, for example, solar filters.

It is quite obvious that the invention is directed toward mammals in general and more particularly toward human beings.

The effective amount of active principle corresponds to the quantity necessary to obtain the desired result, that is to say, to activate cytochrome C, and to increase the cellular energy level, and more generally, to protect the skin and the appendages from external aggressions and to combat cutaneous aging.

According to an advantageous embodiment of the invention, the active principle is present in the compositions of the invention in a concentration between approximately 0.0005 and 500 ppm (parts per million), and preferentially in a concentration between approximately 0.01 and 5 ppm, relative to the total weight of the final composition.

These compositions could come particularly in the form of an aqueous, hydroalcoholic, or oily solution, an oil-in-water or water-in-oil emulsion, or multiple emulsions. They can also come in the form of creams, suspensions, or even powders, adapted to application onto the skin, the mucous membranes, the lips, and/or the appendages. These compositions can be more or less fluid and have the appearance of a cream, a lotion, a milk, a butter, an ointment, a gel, a paste, or a mousse. They can also come in solid form like a stick or be applied on the skin in the form of an aerosol. They can be used as a care product and/or as a makeup product for the skin.

These compositions include, in addition, any additive commonly used in the application domain envisioned, as well as the adjuvants necessary for their formulation, such as solvents, thickeners, diluents, antioxidants, colorants, solar filters, self-bronzing agents, pigments, vehicles, preservatives, perfumes, odor absorbents, active cosmetic or pharmaceutical agents, essential oils, vitamins, essential fatty acids, surfactants, film-forming polymers, etc.

In any case, the professional will take care that these adjuvants, as well as their proportions, are chosen in such a way as not to harm the advantageous properties studied in the composition according to the invention. These adjuvants can, for instance, correspond to 0.01 to 20% of the total weight of the composition. When the composition of the invention is an emulsion, the fatty phase may represent 5 to 80% by weight and preferably 5 to 50% by weight relative to the total weight of the composition. The emulsifiers and co-emulsifiers used in the composition will be chosen from among those traditionally used in the domain considered. For example, they may be used in a proportion from 0.3 to 30% by weight relative to the total weight of the composition.

By means of its particular activities, the active principle according to the invention could be used advantageously in a cosmetic composition or for the preparation of a pharmaceutical composition.

In particular, the active principle according to the invention could be used advantageously in a cosmetic composition intended to combat in a preventive and/or curative manner the manifestations of cutaneous aging and, more specifically, to combat and/or prevent photo-induced aging (photo-aging). "Cutaneous manifestations of aging" is understood to be any alteration of the external appearance of the skin and appendages due to aging, such as, for example, wrinkles and fine wrinkles, shriveled skin, flabby skin, thin skin, lack of elasticity and/or tonus of the skin, dull skin without a glow or pigmentation spots on the skin, fading in hair color or spots on the nails, as well as any internal alteration of the skin that is not manifested systematically by an altered external appearance, such as, for example, any internal degradation of the skin following an exposure to ultraviolet (UV) rays. The active principle according to the invention, or the composition containing it, will allow for combating, in particular, the loss of elasticity and firmness of the skin.

The active principle according to the invention may be used advantageously in a cosmetic composition for protecting the skin and the appendages against all types of external aggressions. The use of the active principle, or of a composition containing it, will allow the skin and the appendages to be protected and to better resist environmental stresses.

The expression "external aggressions" is understood to be aggressions which the environment can produce. By way of example, aggressions may be cited such as pollution, UV rays, or even products of an irritating nature such as surfactants, preservatives, and perfumes. Pollution is also understood to be both "outdoor" pollution due, for example, to Diesel-fuel particles, ozone, or heavy metals, as well as "indoor" pollution, which may be due, in particular, to the emissions of the solvents of paint, glue, or wallpaper (such as toluene, styrene, xylene, or benzaldehyde), or even cigarette smoke.

The active principle according to the invention may be advantageously used in a cosmetic composition or for preparing a pharmaceutical composition, as a photo-protective agent and, more particularly, as a so-called "secondary" photo-protective agent. Primary photo-protective agents are, in effect, differentiated from secondary photo-protective agents. Primary photo-protective agents are substances that exert a physical power: they are in a position to absorb UV rays and release it in the form of heat in order to protect the skin. Secondary photo-protective agents are substances that generally have a biological effect; they are, for example, agents capable of limiting the damage caused to the DNA and to the membranes by UV rays penetrating into the skin.

The invention again is related to use in a cosmetic composition of an effective quantity of active principle according to the invention to increase intracellular ATP synthesis of the cells of the skin.

The invention also has, as an object, use in a cosmetic composition of an effective quantity of active principle according to the invention to prevent damage caused to the skin by exposure to the sun or exposure to ionizing radiation during radiotherapy.

The invention also has, as an object, use in a cosmetic composition of an effective quantity of active principle according to the invention to stimulate the mitochondria, particularly in areas of the body exposed to UV rays.

The invention again is related to use in a cosmetic composition of an effective quantity of active principle as described previously to protect the skin from damage caused by free radicals.

In addition, the invention again consists of the use of an effective quantity of active principle, as described previously, for preparing a pharmaceutical composition intended to prevent or to combat pathologies linked to mitochondrial dysfunctions, such as certain neuromuscular or cardiac degenerations, type II diabetes, or certain pathologies of aging.

Finally, the invention again consists of a cosmetic-treatment procedure intended to stimulate the defenses and to protect the skin and the appendages from external aggressions and to combat cutaneous aging, characterized by the application onto the skin or the appendages to be treated of a composition containing an effective quantity of active principle according to the invention.

Specific embodiments of this cosmetic-treatment procedure also result from the preceding description. Other advantages and characteristics of the invention will be more apparent upon reading the examples given by way of illustration and non-restrictive.

Example 1

Disclosure of the Stimulating Effect of the SEQ ID No. 2 Peptide on the Synthesis of Intracellular ATP The aim of this study was to determine the effect of the SEQ ID No. 2 peptide on the synthesis of ATP produced by the mitochondria.

Protocol: This study was conducted using an ATP Bioluminescence Assay Kit HS II (Roche Applied Science). Dermal fibroblasts were treated with a 1% solution of a 50 ppm solution containing the SEQ ID No. 2 peptide, representative of the peptide family according to the invention, for a period of 1 to 3 hours. At the end of incubation, the tubes were rinsed with 2 ml of cold PBS before adding 250 µl of a lysis buffer provided in the kit. The cells of each tubes were then scraped up and collected in 14-ml tubes. Each tube was rinsed with 2×500 μl of cold PBS and the whole was collected again in the respective tubes. Starting with these samples, a dilution to 1/12,000 was achieved in the cold PBS before each reading. The ATP measurement was performed on these samples: 50 μl of this dilution was placed in a LUMA® cuvette and 50 μl of luminol was added. After 10 seconds, the luminescence reading was begun. The values were standardized relative to the quantity of proteins for each sample. The measurements were made using the Biocounter M2010A LUMA®/3M equipment.

Results: The ATP measurements showed that there was a 41% increase in the amount of intracellular ATP after one hour and 27% after 3 hours in the cells treated with the SEQ ID No. 2 peptide, compared to the untreated cells.

Conclusion: The sequence of SEQ ID No. 2 peptide significantly increases the energy level of cutaneous cells as well as fibroblasts and more generally stimulates the mitochondrial functions.

Example 2

Disclosure of the Activator Effect of the SEQ ID No. 2 Peptide on the Expression of Cytochrome C The aim of this study was to determine the effect of the SEQ ID No. 2 peptide on the expression of cytochrome C. For this, the quantity of cytochrome C was evaluated by the immunotransfer (or Western Blot) technique.

Protocol: Human dermal fibroblasts were treated with a 1% solution of a 50-ppm SEQ ID No. 2 peptide mother-solution for 72 hours. The cells were then lysed and homogenized by sonication, then centrifuged for 10 minutes at 1000 g. The samples, standardized for their protein concentration (BCA measurement kit, Pierce) were subjected to electrophoresis on 4-12% bis-tris gel (INVITROGEN™). After electro-transfer, the membranes were incubated overnight with an anticytochrome C antibody, diluted to 1/500 (mouse monoclonal anti-cytochrome C, Tebu). A secondary antibody, coupled to the peroxidase and diluted to 1/5000 was then used (peroxidase conjugated F(ab')2, goat antimouse, Immunotech). The chemiluminescent signal was then quantified using the Supersignal West Femto Trial kit and read in a reading chamber (MultiImage Light Cabinet, Immunotech Corporation).

Results: A clear increase was observed in the expression of cytochrome C in the fibroblasts treated with the SEQ ID No. 2 peptide.

Conclusions: The SEQ ID No. 2 peptide, in a concentration of 0.05 ppm, strongly stimulates the expression of cytochrome C in cutaneous cells and more generally the mitochondrial functions.

Example 3

Disclosure of the Activator Effect of the SEQ ID No. 2 Peptide on the Enzymatic Activity of Cytochrome Oxidase The aim of this study was to determine the effect of the SEQ ID No. 2 peptide on mitochondrial activity. For this, the total enzymatic (mitochondrial) activity of cytochrome oxidase was measured.

Protocol: Normal human fibroblasts were treated with a 1% solution of a 50-ppm solution containing the SEQ ID No. 2 peptide, representative of the peptide family according to the invention, for 3 hours and 24 hours. The cells were collected, rinsed, and then lysed by sonication. A first centrifuging was performed to eliminate the principal cellular debris, and the supernatant was then centrifuged again at 10,000 g for 10 minutes. The enzymatic activity was measured in the supernatant and/or in the second residue, by a biochemical method using the Cytocox 1 kit (Sigma-Aldrich), then standardized for protein content (measured with the BCA kit, Pierce).

Results: The measurements showed that there was a 150% increase in enzymatic activity of cytochrome oxidase after 3 hours and a 750% increase 24 hours after application of the SEQ ID No. 2 peptide, compared with untreated cells.

Conclusion: The SEQ ID No. 2 peptide, in a concentration of 0.05 ppm, strongly stimulates the enzymatic activity of cytochrome oxidase, and more generally mitochondrial activity, in cutaneous cells.

Example 4

Disclosure of the Protective Effect of the SEQ ID No. 2 Peptide on the Mitochondrial Membrane Potential The aim of this study was to determine the protective effect of the SEQ ID No. 2 peptide with respect to dermal fibroblast mitochondria subjected to an oxidative stress caused by oxygenated water ($H_2O_2$) or UVB irradiation. A marker for the membrane potential of mitochondria (JC-1) was used for this. JC-1 is a marker that emits different fluorescences depending on the level of polarization of the mitochondrial membrane.

Protocol: Human dermal fibroblasts were treated with a 1% solution of a 50-ppm SEQ ID No. 2 peptide mother-solution for 96 hours and then subjected to an oxidative stress caused by 2 mM of $H_2O_2$ for 30 min. or to UVB irradiation at 50 mJ/cm$^2$. Controls not treated with the peptide or $H_2O_2$ or not irradiated were performed under the same conditions. At the end of the experiment, the cells were washed, fixed, and subjected to marking with a 0.2 μg/ml solution of JC-1 MOLECULAR PROBES®) in order to disclose the membrane potential of the mitochondria.

Results: In the fibroblasts treated with the SEQ ID No. 2 peptide, the mitochondria exhibited a red fluorescence (aggregated JC-1), an indication of an elevated membrane potential, greater than in the control cells. The fibroblasts irradiated or subjected to an oxidative stress had mitochondria that fluoresced little in the red and mainly in the green (monomeric JC-1), an indication of an alteration in the mitochondrial membrane potential. Under these last conditions, the application of the SEQ ID No. 2 peptide led to observation of a more marked red fluorescence.

Conclusions: The application of the SEQ ID No. 2 peptide causes an increase in the membrane potential of mitochondria. On the other hand, the SEQ ID No. 2 peptide effectively protects the mitochondria of cutaneous cells subjected to an oxidative stress or to UVB radiation.

Example 5

Preparation of Compositions

| Trade name | International Nomenclature of Cosmetic Ingredients (INCI) names | % W/W |
|---|---|---|
| PHASE A | | |
| Demineralized water | Aqua (water) | In sufficient quantity |
| PEMULEN ® TR-1 | Acrylates/C10-30 alkyl acrylate cross-polymer | 0.40 |
| Glycerine | Glycerin | 3.00 |
| NIPASTAT ® Sodium | Sodium methylparaben (and) sodium ethylparaben (and) sodium butylparaben (and) sodium propylparaben (and) sodium isobutylparaben | 0.15 |
| PHASE B | | |
| PARSOL ® MCX | Ethylhexyl methoxycinnamate | 7.50 |
| EUSOLEX ® 4360 | Benzophenone-3 | 3.00 |
| PARSOL ® 1789 | Butyl methoxydibenzoyl-Methane | 2.00 |
| MYRITOL ® 318 | Caprylic/capric triglyceride | 4.00 |
| EMULGADE ® SEV | Hydrogenated palm glycerides (and) ceteareth-20 (and) ceteareth-12 (and) cetearyl alcohol | 5.00 |
| Propylparaben | Propylparaben | 0.15 |
| NACOL ® 16-98 | Cetyl alcohol | 1.00 |
| PHASE C | | |
| TEA | Triethanolamine | 0.20 |
| PHASE D | | |
| SEQ ID No. 2 peptide | | 3 ppm |
| Perfume | Perfume (fragrance) | In sufficient quantity |
| Colorant | | In sufficient quantity |

The constituents of phase A and of phase B were heated separately to a temperature between 70° C. and 75° C. Phase B was emulsified in phase A while stirring. Phase C was added, at 45° C., while increasing the stirring. Phase D was then added when the temperature was below 40° C. Cooling was continued down to 25° C. with brisk stirring.

| Trade name | INCI names | % W/W |
|---|---|---|
| PHASE A | | |
| MONTANOV ™ L | C14-22 alcohols (and) C12-20 alkyl glucoside | 3.00 |
| Waglinol 2559 | Cetearyl isononanoate | 4.00 |
| TEGOSOFT ® TN | C12-15 alkyl benzoate | 3.00 |
| Apricot kernel oil | Prunus armeniaca (apricot) kernel oil | 2.00 |
| Avocado oil | Persea gratissima (avocado) Oil | 1.00 |
| ABIL ® 350 | Dimethicone | 1.00 |
| PHASE B | | |
| Demineralized water | Aqua (water) | In sufficient quantity |
| PHASE C | | |
| SIMULGEL ™ EG | Sodium acrylate/acryloyl-dimethyl taurate copolymer (and) isohexadecane (and) polysorbate 80 copolymer (and) polysorbate 80 | 0.4 |
| PHASE D | | |
| PHENONIP ® | Phenoxyethanol (and) methylparaben (and) ethylparaben (and) butylparaben (and) propylparaben (and) isobutylparaben ethylparaben and propylparaben and butylparaben | 0.30 |
| GERMALL ® 115 | Imidazolidinyl urea | 0.20 |
| PHASE E | | |
| SEQ ID No. 2 peptide | | 0.1 ppm |

Prepare phase A while stirring. Incorporate the xanthan gum gradually with dispersant stirring. Phases C and D will be incorporated once the gel has set. Phase E, prepared in advance to the point of perfect DHA dissolution, will then be added. Adjust the pH if necessary to 4-4.5. Color and perfume.

| Trade name | INCI names | % W/W |
|---|---|---|
| PHASE A | | |
| MONTANOV ™ 68 | Cetearyl alcohol (and) cetearyl glucoside | 6.00 |
| Squalane | Squalane | 3.00 |
| CETIOL ® SB 45 | Butyrospermum parkii (Shea butter) | 2.00 |
| Waglinol 250 | Cetearyl ethylhexanoate | 3.00 |
| Amerchol L-101 | Mineral oil (and) lanolin Alcohol | 2.00 |
| ABIL ® 350 | Dimethicone | 1.50 |
| BHT | Butylhydroxytoluene | 0.01 |
| Coenzyme Q10 | Ubiquinone | 0.10 |
| PHASE B | | |
| Avocado oil | Persea gratissima (avocado) Oil | 1.25 |
| PHENONIP ® | Phenoxyethanol (and) methylparaben (and)\ ethylparaben (and) butylparaben (and) propylparaben (and) isobutylparaben | 0.75 |
| PHASE C | | |
| Demineralized water | Aqua (water) | In sufficient quantity |
| Butylene glycol | Butylene glycol | 2.00 |
| GLUCAM ™ E10 | Methyl gluceth-10 | 1.00 |
| Allantoin | Allantoin | 0.15 |
| CARBOPOL ® Ultrez 10 | Carbomer | 0.20 |
| PHASE D | | |
| TEA | Triethanolamine | 0.18 |
| PHASE E | | |
| SEQ ID No. 2 peptide | | 0.5 ppm |
| GP4G ® | Water (and) Artemia extract | 1.50 |
| COLLAXYL ® | Water (and) butylene glycol (and) hexapeptide-9 | 3.00 |
| PHASE F | | |
| Perfume | Perfume (fragrance) | In sufficient quantity |
| Colorant | | In sufficient quantity |

Prepare and melt phase A at 65-75° C. Heat phase C to 65-70° C. Phase B is added to phase A just before emulsifying A in B. At about 45° C., the carbomer is neutralized by the addition of phase D. Phase E is then added with light stirring, and cooling is continued to 25° C. Phase F is then added, if desired.

| Trade name | INCI names | % W/W |
|---|---|---|
| PHASE A | | |
| EMULIUM DELTA ® | Cetyl alcohol (and) glyceryl stearate (and) PEG-75 stearate (and) ceteth-20 (and) steareth-20 | 4.00 |
| Lanette O | Cetearyl alcohol | 1.50 |
| DC200 FLUID ®/100 cs | Dimethicone | 1.00 |
| DUB 810C | Coco caprylate/caprate | 1.00 |
| DPPG | Propylene glycol dipelargonate | 3.00 |
| DUB DPHCC | Dipentaerythrityl hexacaprylate/hexacaprate | 1.50 |
| CEGESOFT ® PS 6 | Vegetable oil | 1.00 |
| Vitamin E | Tocopherol | 0.30 |
| PHENONIP ® | Phenoxyethanol (and) methylparaben (and) ethylparaben (and) butylparaben (and) propylparaben (and) isobutylparaben | 0.70 |

| Trade name | INCI names | % W/W |
|---|---|---|
| PHASE B | | |
| Demineralized water | Aqua | In sufficient quantity, 100 |
| Glycerine | Glycerin | 2.00 |
| CARBOPOL ® ETD 2020 | Acrylates/C10-30 alkyl acrylate cross-polymer | 0.15 |
| Keltrol CG-BT | Xanthan gum | 0.30 |
| PHASE C | | |
| Sodium hydroxide (10% solution) | Sodium hydroxide | 0.30 |
| PHASE D | | |
| Demineralized water | Aqua | 5.00 |
| STAY-C ® 50 | Sodium ascorbyl phosphate | 0.50 |
| PHASE E | | |
| Butylene glycol | Butylene glycol | 2.00 |
| Dekaben CP | Chlorphenesin | 0.20 |
| PHASE F | | |
| GP4G ® | Water (and) *Artemia* extract | 1.00 |
| SEQ ID No. 2 peptide | | 5 ppm |

Prepare phase A and heat to 75° C. while stirring. Prepare phase B while dispersing the CARBOPOL® and then the xanthan gum while stirring. Let rest. Heat to 75° C.

The invention claimed is:

1. A composition, comprising:
   an active principle comprising a peptide capable of activating cytochrome C,
   said peptide consisting of 3 to 5 amino acid residues and a sequence according to the following formula:

$R_1-X_1-X_2-X_3-X_4-X_5-R_2$ wherein,
   $X_1$ is tyrosine,
   $X_2$ is leucine,
   $X_3$ is lysine,
   $X_4$ is threonine, serine, lysine, arginine, or no amino acid,
   $X_5$ is valine, alanine, tyrosine, methionine, or no amino acid,
   $R_1$ represents a primary amine function of an N-terminal amino acid, free or substituted with a protector group selected form the group consisting of: an acetyl group, a benzoyl group, a tosyl group, and a benzyloxycarbonyl group, and
   $R_2$ represents a hydroxyl function of a carboxylic acid of a C-terminal amino acid, free or substituted with a protector group selected from the group consisting of: an alkyl chain of $C_1$ to $C_{20}$, an $NH_2$ group, NHY group, and NYY group, with Y representing an alkyl chain of $C_1$ to $C_4$; and
   a physiologically acceptable medium.

2. The composition according to claim 1, wherein said peptide consists of a sequence selected from the group consisting of:

(SEQ ID No. 1)    Tyr-Leu-Lys-Lys-Ala;
   (SEQ ID No. 2)    Tyr-Leu-Lys-Lys-Ala-NH₂;
   (SEQ ID No. 3)    Tyr-Leu-Lys-Lys-NH₂;
   and
   (SEQ ID No. 4)    Tyr-Leu-Lys.

3. The composition according to claim 2, wherein said peptide consists of the sequence SEQ ID NO: 1.

4. The composition according to claim 2, wherein said peptide consists of the sequence SEQ ID NO: 2.

5. The composition according to claim 1, wherein said peptide possesses at least one functional group protected by a protector group, said protector group is at least one of (i) an acylation or an acetylation of the amino-terminal end and (ii) an amidation or an esterification of the carboxy-terminal end.

6. The composition according to claim 1, wherein said active principle is present at a concentration between 0.0005 ppm and 500 ppm by total weight of said composition.

7. The composition according to claim 6, wherein said active principle is present at a concentration between 0.01 ppm and 5 ppm by total weight of the composition.

8. The composition according to claim 1, wherein said active principle is solubilized in advance in a solvent selected from the group consisting of: water, glycerol, ethanol, propylene glycol, butylene glycol, dipropylene glycol, ethoxylated or propoxylated diglycols, cyclic polyols, vaseline, a vegetable oil, and mixtures thereof.

9. The composition according to claim 1, wherein said composition is in a form adapted for topical application.

10. The composition according to claim 1, further comprising at least one active agent which promotes the action of said active principle.

11. The composition according to claim 10, wherein said active agent is selected from the group consisting of: active agents having an antioxidant action, active agents stimulating synthesis of dermal macromolecules, and active agents stimulating energy metabolism.

12. A method of preparing a cosmetic composition or a pharmaceutical composition, comprising adding an effective amount of an active principle to a cosmetically or pharmaceutically acceptable medium,
   said active principle comprising a peptide capable of activating cytochrome C,
   said peptide consisting of 3 to 5 amino acid residues and a sequence according to the following formula:

$R_1-X_1-X_2-X_3-X_4-X_5-R_2$ wherein,
   $X_1$ is tyrosine,
   $X_2$ is leucine,
   $X_3$ is lysine,
   $X_4$ is threonine, serine, lysine, arginine, or no amino acid,
   $X_5$ is valine, alanine, tyrosine, methionine, or no amino acid,
   $R_1$ represents a primary amine function of an N-terminal amino acid, free or substituted with a protector group selected form the group consisting of: an acetyl group, a benzoyl group, a tosyl group, and a benzyloxycarbonyl group, and
   $R_2$ represents a hydroxyl function of a carboxylic acid of a C-terminal amino acid, free or substituted with a protector group selected from the group consisting of: an alkyl chain of $C_1$ to $C_{20}$, an $NH_2$ group, NHY group, or NYY group, with Y representing an alkyl chain of $C_1$ to $C_4$.

13. A method of reducing the effects of external aggression on skin and appendages, comprising administering, before and/or after exposure to the aggression, to a subject in need thereof the composition according to claim 1, wherein said composition comprises an effective amount of the active principle and a cosmetically acceptable medium.

14. A method of reducing the effects of or treating skin damage and appendage damage caused by UV radiation, comprising administering to a subject in need thereof the composition according to claim 1, wherein said composition comprises an effective quantity of the active principle and a cosmetically acceptable medium.

15. A method of stimulating mitochondria, comprising administering to a subject in need thereof the composition according to claim 1, wherein said composition comprises an effective quantity of the active principle and a cosmetically acceptable medium.

16. A method of increasing synthesis of intracellular ATP in skin cells, comprising administering to a subject in need thereof the composition according to claim 1, wherein said composition comprises an effective quantity of the active principle and a cosmetically acceptable medium.

17. A method of reducing the effects of or treating cutaneous signs of aging and/or photo-aging, comprising administering to a subject in need thereof the composition according to claim 1, wherein said composition comprises an effective quantity of the active principle and a cosmetically acceptable medium.

18. A method of stimulating defenses of skin and appendages from external aggressions, comprising topically applying onto the skin or appendages of a subject in need thereof the composition according to claim 1, wherein said composition comprises an effective quantity of the active principle and a cosmetically acceptable medium.

* * * * *

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Tyr Leu Lys Lys Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 2

Tyr Leu Lys Lys Ala
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION
```

```
<400> SEQUENCE: 3

Tyr Leu Lys Lys
1

<210> SEQ ID NO 4
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 4

Tyr Leu Lys
1
```